United States Patent [19]

Franke

[11] 4,021,672
[45] May 3, 1977

[54] DENTAL X-RAY DIAGNOSTIC INSTALLATION

[75] Inventor: Kurt Franke, Erlangen, Germany

[73] Assignee: Siemens Aktiengesellschaft, Berlin & Munich, Germany

[22] Filed: Oct. 1, 1975

[21] Appl. No.: 618,614

[30] Foreign Application Priority Data

Oct. 2, 1974 Germany .......................... 2447075

[52] U.S. Cl. ............................... 250/402; 250/409; 250/413

[51] Int. Cl.² .......................................... H05G 1/30

[58] Field of Search .......... 250/401, 402, 408, 409, 250/413, 414, 416

[56] References Cited

UNITED STATES PATENTS 3,536,913  10/1970  Huchel .............................. 250/439
3,546,461  12/1970  Craig ................................. 250/416

Primary Examiner—Craig E. Church
Attorney, Agent, or Firm—Hill, Gross, Simpson, Van Santen, Steadman, Chiara & Simpson

[57] ABSTRACT

A dental X-ray diagnostic apparatus in which the setting of the adjustable exposure value, is automatically carried out. A ray detector is applied to the film carrier, which delivers an electrical signal in conformance with the dose rate when it is struck by X-radiation and which, together with the setting means and a dose rate regulator, is connected to an automatic exposure timer in such a manner whereby the adjustable exposure value is influenced by the output signal of the ray detector for the purpose of effecting maintaining constant the dose rate to a value producing an optimum degree of film darkening, and that there is positioned a sample-and-hold circuit between the regulator and the ray detector which stores this signal at a value corresponding to one of the lowest dose rates during a time which is required for the exposure of a plurality of teeth, and whose output signal is transmitted to the actual value input of the dose rate regulator.

3 Claims, 3 Drawing Figures

DENTAL X-RAY DIAGNOSTIC INSTALLATION

FIELD OF THE INVENTION

The present invention relates to a dental X-ray diagnostic installation.

DISCUSSION OF THE PRIOR ART

In order to elucidate the concept of the invention, a known X-ray diagnostic installation is schematically illustrated in FIG. 1 of the drawings. The known prior art installation contains an X-ray tube within a housing 1 which is vertically adjustably supported on a carrier 2. The X-ray film in a semicircularly curved cassette is fastened to a cassette holder 3. The cassette holder 3 is fastened to a carrier 4. The carriers 2 and 4 are each connected with a support arrangement 5. Located between the cassette holder 3 and the X-ray tube housing 1 is a patients' head support 6. As viewed in the ray direction, a slit diaphragm is arranged in front of the casette holder 3.

For effecting the preparation of a tooth-or jaw charting planigraphic or tomographic exposure, the head of the patient is retained in the support arrangement 6. During an exposure, the X-ray tube housing 1 together with the X-ray tube and the cassette holder 3, moves with the film which is supported thereon about the head of the patient. The X-ray tube housing 1, as well as also the cassette holder 3 are hereby rotated about a vertical axis so that the X-rays always strike at a right angle against the teeth and so as to form an always equal remaining spacing between the tooth row and the film. During the movement of the cassette holder 3 and the X-ray tube housing about the head of a patient, the teeth sequentially and the jaw are reproduced on the film.

In the known X-ray diagnostic installation of the above-described type, the exposure time is rigidly pregiven by means of the timing or run-down mechanism which is constituted of a unit formed by the X-ray tube and film carrier. For determining the film darkening, there must be adjusted the X-ray tube voltage. The quality of an exposure depends thereby upon the correct feel or sense of the operating personnel of the installation.

SUMMARY OF THE INVENTION

Accordingly, it is an object of the present invention to provide a dental X-ray diagnostic apparatus of the above-described type, in which the setting of the adjustable exposure value, in the known installation consisting of the X-ray tube voltage, is automatically carried out.

The foregoing object is inventively attained in that a ray detector is applied to the film carrier, which delivers an electrical signal in conformance with the dose rate when it is struck by X-radiation and which, together with the setting means and a dose rate regulator, is connected to an automatic exposure timer in such a manner whereby the adjustable exposure value is influenced by the output signal of the ray detector for the purpose of effecting maintaining constant the dose rate to a value producing an optimum degree of film darkening, and that there is positioned a sample-and-hold circuit between the regulator and the ray detector which stores this signal at a value corresponding to one of the lowest dose rates during a time which is required for the exposure of a plurality of teeth, and whose output signal is transmitted to the actual value input of the dose rate regulator.

The invention takes cognizance of the fact that a known automatic X-ray timer for tomographic X-ray apparatus, in which the exposure time is similarly fixedly pregiven, may also be employed in a dental X-ray diagnostic installation of the above-described type. Influenced by the output signal of the ray detector preferably is hereby the X-ray tube voltage as an adjustable exposure value. When the ray detector lies opposite the teeth of the patient during the preparation of an exposure, then the dose rate at the ray detector fluctuates considerably during an exposure, which leads to a variation of the exposure voltage within wide limits and to a poorly contrasted image, when there is no provision of a sample-and-hold circuit which stores the output signal of the ray detector corresponding to the value of one of the lowest dose rates during a time which is required for the exposure of a plurality of teeth, and whose output signal is transmitted to the actual value input of the dose rate regulator.

Another solution of the object as set forth by the present invention lies in that the ray detector is struck by the X-radiation during an exposure, which passes through at least one jaw of the patient. Since, it this instance, there are encountered substantially lower dose rate fluctuations at the ray detector, the above-mentioned sample-and-hold circuit may thus be eliminated.

BRIEF DESCRIPTION OF THE DRAWINGS

Further advantages and details of the invention may now be ascertained from the following description of an exemplary embodiment thereof, taken in conjunction with the accompanying drawings; in which.

DETAILED DESCRIPTION

Figure 1:
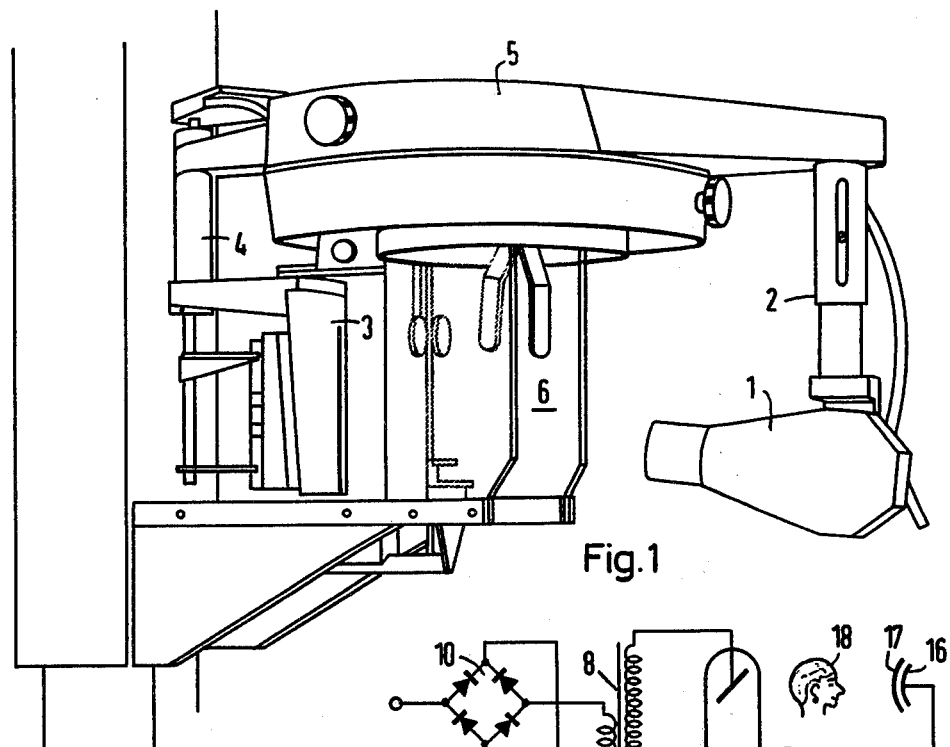
FIG. 1 schematically illustrates a known X-ray diagnostic installation.
Figure 2:
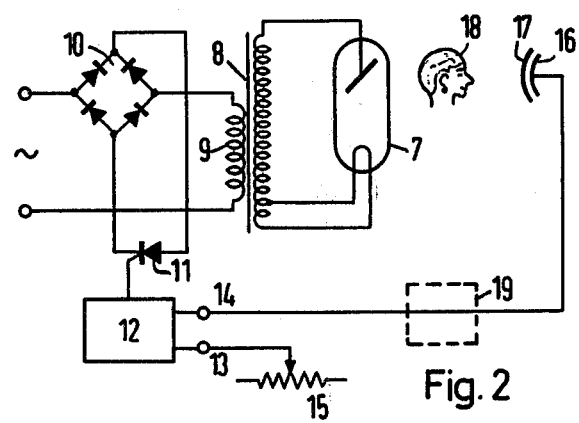
FIG. 2 illustrates a circuit diagram of an X-ray diagnostic installation constructed pursuant to the invention.
Figure 3:
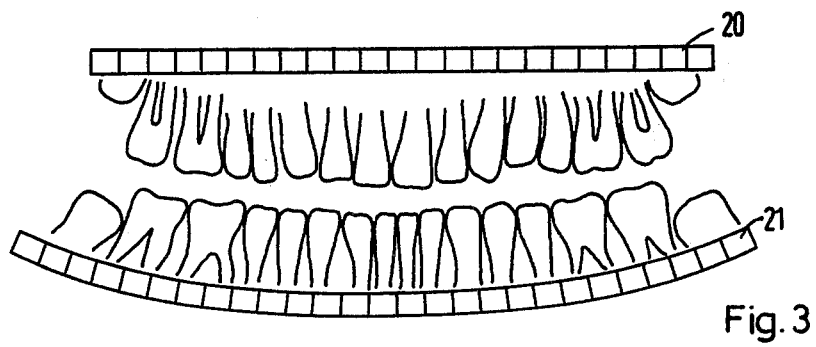
FIG. 3 illustrates, in a schematic representation, an X-ray picture which has been prepared with the aid of a dental diagnostic installation pursuant to the invention, and wherein there is, in an exemplary manner, indicated the location of the ray detector.

Referring now in detail to the present invention as represented by FIGS. 2 and 3, there is illustrated in FIG. 2 an X-ray tube 7 which is located within a housing 1, and which is supplied from a secondary winding of a high-voltage transformer 8 with high-voltage and filament voltage. The primary winding 9 of the high-voltage transformer 8 is connectable to a power supply through the intermediary of a diode bridge 10, having a thyristor 11 located in the direct current branch thereof. The thyristor 11 receives trigger impulses from a dose rate regulator 12 which possesses a reference value input 13 and an actual value input 14. The reference value signal is tapped off from a setting means 15, while the actual value signal for the dose rate is delivered by a ray detector 16 which lies behind the X-ray film 17 supported on the film carrier 3. The head 18 of a patient lies between the X-ray tube 7 and the X-ray film 17.

The dose rate regulator 12 receives a signal at its input 13 which provides an optimum film darkening at the fixedly pregiven exposure time of, for example, 15 seconds. It so sets the firing of the trigger impulse of the thyristor 11 in dependence upon the difference between this signal and the actual value signal at the input 14, so that the dose rate is maintained constant.

When the ray detector 16 lies in a zone in which it is struck by that X-radiation which passes through the teeth of the patient, then the dose rate fluctuates strongly at the detector and, consequently, the signal at the input 14 of the regulator 12. For counter-balancing the fluctuations of this signal, pursuant to the invention there may be connected a sample-and-hold circuit 19 between the input 14 and the detector 16, which stores the output signal of the X-ray detector 16 at a value corresponding to one of the lowest dose rates for a period of time which is required for the exposure of a plurality of teeth. For example, the sample-and-hold circuit 19 may possess a storage period which approximately corresponds to the period of time required for the exposure of three teeth. In that manner the X-ray tube voltage is prevented from varying within wide limits by means of the regulator 12, which would exert itself in an undesirable manner on the picture quality.

The sample-and-hold circuit 19 also effects that, after the exposure of three tooth batches, the lowest value of the dose rate occurring hereby is compared with the reference value at the input 13, and the dose rate is varied for the purpose of affording a correlation of the actual value signal of the sample-and-hold circuit to the reference value signal through intermediary of the thyristor 11. After three more tooth batches, a new regulation is effected. This sequence repeats itself until the exposure is completed.

The sample-and-hold circuit 19 may be eliminated when the ray detector 16 is located in a position behind the X-ray film 17, in which it is struck by X-radiation passing through at least one jaw during the entire duration of an exposure. It is thereby assumed that the transmissivity of the teeth, and that of the lower or upper jaws of the same patient, is approximately equal. Since in an exposure there occurs only minute density fluctuations when the X-rays scan a jaw, in this manner there is then possible to effect a direct regulation of the dose rate.

FIG. 3 illustrates the arrangement of the ray detector for this case in connection with an X-ray exposure. FIG. 3 basically assumes that the ray detector consists of a row of measuring areas which are connected in parallel, and of which one portion struck by the radiation penetrating through the upper jaw, and the other portion by the radiation penetrating through the lower jaw. The measuring areas which are associated with the upper jaw are so arranged that they generally assume the position 20 shown in FIG. 3, whereas the measuring areas which are associated with the lower jaw are so arranged that they generally assume the position 21 shown in FIG. 3. Within the scope of the invention it may be sufficient when measuring areas are associated with only one jaw.

In the illustrated exemplary embodiment, by means of the triggering timepoints of the thyristor 11, the X-ray tube voltage as well as also the X-ray tube current are varied for effectuating the regulation of the dose rate. Within the scope of the invention it is also possible to only influence one of these parameters, in particular, the X-ray tube voltage.

The dose rate regulator 12 may consist of a differential amplifier for the difference between the signals at the inputs 13 and 14.

While there has been shown what is considered to be the preferred embodiment of the invention, it will be obvious that modifications may be made which come within the scope of the disclosure of the specification.

What is claimed is:

1. In a dental X-ray diagnostic installation including a unit rotatable about vertical axes, said unit being constituted of an X-ray tube and film carrier, and a support for retaining a patients' head between said X-ray tube and film carrier; a timing mechanism in said X-ray tube and film carried unit for preparing charting exposures at a fixedly preset exposure time; and setting means for adjusting at least one exposure value, the improvement comprising: a ray detector being applied to said film carrier; a dose rate regulator; an automatic exposure timer; said ray detector being interconnected with said setting means, dose rate regulator and automatic exposure timer, said ray detector delivering a signal corresponding to the X-ray dose rate so that the adjustable exposure value is influenced by the output signal of said ray detector to a value for maintaining constant the dose rate and providing an optimum film darkening, and a sample-and-hold circuit being connected intermediate said dose rate regulator and ray detector for storing said signal at a value corresponding to one of the lowest dose rates for a period of time which is required for the exposure of a plurality of teeth, said circuit having the output signal thereof transmitted to an actual value input of said dose rate regulator.

2. An X-ray diagnostic installation as claimed in claim 1, said sample-and-hold circuit having a storage time generally corresponding to the time required for the exposure of three teeth.

3. In an X-ray diagnostic installation for making radiographs of teeth and including a unit rotatable about vertical axes, said unit being constituted of an X-ray tube and film carrier, and a support for retaining a patients' head between said X-ray tube and film carrier, a timing mechanism in said X-ray tube and film carrier unit for preparing charting X-rays at a fixedly preset exposure time; and setting means for adjusting at least one exposure value, the improvement comprising: a ray detector mounted on said film carrier and positionable along the patients' jaw and in a location displaced from the line of teeth to be examined so as to be exposed to radiation from said X-ray tube directed at teeth adjacent said jaw; a dose rate regulator; and an automatic exposure timer; said ray detector being interconnected with said setting means, dose rate regulator and automatic exposure timer, said ray detector being located on said film carrier in a position so as to be struck by radiation passing through at least one jaw of the patient for the entire duration of an exposure to thereby deliver an electrical signal corresponding to the dose rate whereby the adjustable exposure value is influenced by the output signal of said ray detector to a value for maintaining constant the dose rate and providing an optimum film darkening; said output signal of said ray detector directly controlling the dose rate.

* * * * *